United States Patent
Liu et al.

(10) Patent No.: US 12,419,912 B2
(45) Date of Patent: *Sep. 23, 2025

(54) EPSTEIN-BARR VIRUS (EBV) ANTIGEN COMPOSITES AND DENDRITIC CELL (DC)-BASED VACCINE, AND USE THEREOF

(71) Applicants: KOUSAI Bio Co., Ltd, Shanghai (CN); Helen Liu, Shanghai (CN)

(72) Inventors: Helen Liu, Shanghai (CN); Ze Yin, Shanghai (CN)

(73) Assignees: Helen Liu, Shanghai (CN); KOUSAI Bio Co., Ltd, Shanghai (CN)

( * ) Notice: Subject to any disclaimer, the term of this patent is extended or adjusted under 35 U.S.C. 154(b) by 4 days.

This patent is subject to a terminal disclaimer.

(21) Appl. No.: 18/574,764

(22) PCT Filed: Jun. 17, 2022

(86) PCT No.: PCT/CN2022/099296
§ 371 (c)(1),
(2) Date: Dec. 28, 2023

(87) PCT Pub. No.: WO2023/005486
PCT Pub. Date: Feb. 2, 2023

(65) Prior Publication Data
US 2024/0269171 A1    Aug. 15, 2024

(30) Foreign Application Priority Data
Jul. 29, 2021   (CN) .......................... 202110864886.4

(51) Int. Cl.
| | |
|---|---|
| *A61K 35/15* | (2025.01) |
| *A61K 40/19* | (2025.01) |
| *A61K 40/46* | (2025.01) |
| *A61P 31/22* | (2006.01) |
| *C12N 5/0784* | (2010.01) |

(52) U.S. Cl.
CPC .............. *A61K 35/15* (2013.01); *A61K 40/19* (2025.01); *A61K 40/46* (2025.01); *A61P 31/22* (2018.01); *C12N 5/0639* (2013.01)

(58) Field of Classification Search
None
See application file for complete search history.

(56) References Cited

U.S. PATENT DOCUMENTS

2006/0188520 A1*  8/2006  Steinman ............. C07K 14/005
                                                        424/188.1
2011/0306948 A1   12/2011  Decker et al.

FOREIGN PATENT DOCUMENTS

| CN | 110698544 A | 1/2020 |
| CN | 112390860 A | 2/2021 |
| CN | 113521270 A | 10/2021 |
| CN | 114246942 A | 3/2022 |

OTHER PUBLICATIONS

Sharma, 2019, J. Clin. Invest. vol. 129: 1836-1838.*
Sugano, 2001, J. Exp. Clin. Canc. Res. vol. 20: 175-182.*
Laghmouchi, 2019, Cell Ther. Immunother. pp. 1-15.*
Tsai, 2017, Oncotarget, vol. 17: 10238-10254.*
Zyl, 2019, Front. Oncology, vol. 9: 1-11.*
Cechim, 2019, Ann. Braz. Acad. Sci vol. 94: 1-21.*
Puig-Kroger, 2001, Blood. vol. 98: 2175-2182.*
Krakow, 2019, Front. Immunol. vol. 10: 1-14.*
Navabi, 2009, Vaccine, vol. 27: 107-115.*
Wolfgang Herr, et al., Mature dendritic cells pulsed with freeze-thaw cell lysates define an effective in vitro vaccine designed to elicit EBV-specific CD4+ and CD8+ T lymphocyte responses, Blood, 2000, pp. 1857-1864, vol. 96 No. 5, Immunobiology.

* cited by examiner

*Primary Examiner* — Amy E Juedes
(74) *Attorney, Agent, or Firm* — Bayramoglu Law Offices LLC

(57) ABSTRACT

Epstein-Barr virus (EBV) antigen composites and a dendritic cell (DC)-based vaccine, and a use thereof in preparation of a drug for controlling an EBV-associated infectious disease are provided. Patient-derived DCs are stimulated in vitro, loaded with lysates of various types of EBV-infected cells with strong immunogenicity for EBV-associated infectious diseases, and induced into mature dendritic cells (mDCs) by various cytokines and specific agonists, so as to obtain a complete DC-based vaccine with corresponding antigens. The DC-based vaccine can be injected back into the patient to activate the immune system to produce cytotoxic T cells, thereby killing EBV-infected cells, exerting an immunological effect, and improving a life quality of the patient. In addition, the DC-based vaccine can be prepared in about one week with a low cost, is safe, and shows no obvious side effects.

1 Claim, 4 Drawing Sheets

Specification includes a Sequence Listing.

EPSTEIN-BARR VIRUS (EBV) ANTIGEN COMPOSITES AND DENDRITIC CELL (DC)-BASED VACCINE, AND USE THEREOF

CROSS REFERENCE TO THE RELATED APPLICATIONS

This application is the national phase entry of International Application No. PCT/CN2022/099296, filed on Jun. 17, 2022, which is based upon and claims priority to Chinese Patent Application No. 202110864886.4, filed on Jul. 29, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSHSS002_Sequence_Listing.txt, created on 12/08/2023, and is 1,147 bytes in size.

TECHNICAL FIELD

The present disclosure belongs to the technical field of biomedicine, and in particular relates to Epstein-Barr virus (EBV) antigen composites and a dendritic cell (DC)-based vaccine, and a use thereof in preparation of a drug for treating EBV-associated infectious diseases.

BACKGROUND

EBV is a member of the lymphotropic virus genus of the herpesvirus family that contains a 170 kb double-stranded DNA genome, which encodes about 100 genes, including critical genes for viral capsid antigens (VCAs), early antigens (EAs), and nuclear antigens (NAs). EBV, one of the most ubiquitous infectious agents, infects nearly 95% of adults worldwide. EBV persists for the life of a host and causes diseases with regional differences. Infection with EBV usually occurs during childhood and adolescence. EBV infection may develop into a long-term latent condition in general, and may also lead to the generation of various malignant tumors and diseases in humans, such as Burkitt's lymphoma (BL), nasopharyngeal carcinoma (NPC), Hodgkin's lymphoma (HL), non-Hodgkin's lymphoma (NHL), gastric carcinoma (GC), breast cancer (BC), tumors in immunocompromised patients, chronic active EBV (CAEBV) infection, EBV-associated hemophagocytic lymphohistiocytosis (EBV-HLH), and infectious mononucleosis (IM). In addition, EBV can specifically infect B lymphocytes in humans and some primates in vivo or in vitro (in recent years, it has been found that EBV may also infect T lymphocytes, epithelial cells, and natural killer cells, causing EBV-related diseases), and can stimulate the continuous growth of infected cells and cause the infinite passage of cells to allow immortalization, thereby producing lymphoblastoid cell lines (LCLs). LCLs are often used to investigate the occurrence and development of various diseases, which makes it possible to investigate the pathogenesis of some diseases on a large scale for a long time. However, the pathogenic mechanism of EBV is currently not fully understood, and no safe and effective treatment is available for EBV-associated diseases.

EBV has two infection modes, namely, replicative infection and latent infection. During the replicative infection, viral DNA is transcribed to express VCAs and EAs to produce mature viral particles, and host cells undergo lysis and death. The replicative infection is mainly seen in EBV-infected diseases such as IM. During the latent infection, the expression of VCAs and EAs is inhibited, Epstein-Barr nuclear antigens (EBNAs), EBV-encoded small RNAs (EBERs), and latent membrane proteins (LMPs) are mainly expressed, and no new viral particles are produced. The latent infection is mainly seen in EBV-associated malignant tumors. Cells latently infected with EBV have 4 different gene expression types, which are related to different clinical malignant neoplastic diseases. Type I latent infection mainly occurs in tumor cells of endemic Burkitt's lymphoma (eBL), and involves viral products of EBNA-1 and EBER. Type II latent infection involves NPC and Hodgkin's disease (HD), and viral products such as EBNA-1, LMP-1, LMP-2, and EBER are produced in infected cells. Type III latent infection is common in plasmacytic lymphoma cells in immunosuppressed patients, and 6 types of EBNAs, 3 types of LMPs, and 2 types of EBERs at a viral latent infection stage can be detected. Type IV latent infection occurs only in B lymphocytes in healthy virus-carriers, and these cells contain EBNA-1, LMP-2, and EBER-1.

IM is an acute infectious disease caused by EBV. About 50% of immunocompetent people initially infected with EBV undergo typical IM. A pathological change of IM is the benign proliferation of lymphoid cells, and may affect livers, spleens, myocardia, kidneys, adrenal glands, lungs, and central nervous systems (CNSs), which is manifested as abnormal lymphocytic infiltration. Clinically, IM is manifested mainly as fever, angina, hepatomegaly, splenomegaly, lymph node enlargement, and peripheral blood dyslymphocytosis. The prognosis of IM is generally favorable, a fatality rate of IM is 1% to 2%, and IM patients mostly die from complications. However, in a very small number of IM patients, conditions are protracted and recurrent, and may transform into CAEBV infection. It is currently believed that an immune response of T lymphocytes to fight B lymphocytes with EBV infection is a basis for production of various clinical symptoms.

Hemophagocytic syndrome (HPS) can be classified as primary HPS and secondary HPS. The secondary HPS is caused by EBV infection and is known as EBV-associated HPS (EBV-HLH). EBV infection can cause abnormal activation and proliferation of $CD8^+$ T lymphocytes, activation of macrophages, mass production and release of inflammatory cytokines such as interferon (IFN), tumor necrosis factor (TNF), soluble interleukin (IL)-2 receptors, IL-1, IL-6, IL-10, and macrophage colony-stimulating factor (M-CSF), hypercytokinemia (or cytokine storm), histiocytosis, and autophagocytosis of blood cells. A histopathological manifestation of EBV-associated HPS is the proliferation and infiltration of lymphocytes and histiocytes in all organs. The EBV-associated HPS occurs in a course of IM, repeatedly occurs during a CAEBV infection process, and can be found in patients with EBV-positive natural killer (NK)/T-cell lymphoma. Clinical manifestations of EBV-associated HPS include hyperpyrexia, hepatomegaly, splenomegaly, lymph node enlargement, pancytopenia, liver dysfunction, significant increase in lactate dehydrogenase (LDH), triacylglycerol, and ferritin, decrease in fibrinogen, disseminated intravascular coagulation (DIC). The examination of lymph nodes and bone marrow is characterized by the emergence of phagocytosis of erythrocytes and karyocytes by histiocytes. The prognosis of EBV-associated HPS is poor, and there is no safe and effective treatment clinically for EBV-associated HPS, and more than half of EBV-associated HPS patients will die. It is difficult to distinguish EBV-associated HPS from malignant histiocytosis (MH) clinically.

It is currently considered that CAEBV infection is manifested by abnormal EBV antibody increase and EBV DNA increase, and easily develops into lymphoma, virus-associated hemophagocytic syndrome (VAHS), interstitial pneumonia, and CNS disorders, thereby developing into lymphoproliferative disorders (LPDs) causing multiple organ failure (MOF). CAEBV infection can occur at any age, but mainly occurs in children and adolescents. About 50% of patients with CAEBV infection die within 5 years after onset due to serious complications such as liver failure, myocarditis, coronary artery aneurysm (CAA), infection-associated HPS, and hematologic malignancies. EBV can involve various types of lymphocytes at different sites and undergo clonal proliferation, so that CAEBV infection has various clinical manifestations, including prominent manifestations such as persistent or intermittent fever, hepatomegaly, splenomegaly, and lymph node enlargement and other manifestations such as sore throat, lymph node tenderness, anemia, muscle soreness, joint pain, hydroa vacciniforme, and mosquito allergies, which may affect the blood system, the CNS, the digestive system, and the respiratory system. Related complications include HPS, leukemia, and NK/T-cell lymphoma. At present, many countries and regions worldwide still adopt the following diagnostic criteria proposed by Straus in 1988: (1) onset symptoms of EBV infection last for 6 months or more, and a titer of an anti-EBV antibody is abnormal (including: anti-VCA-IgG antibody ratio≥1:5120, anti-EA antibody ratio≥1:640, or anti-EBNA antibody ratio<1:2); (2) major organs are damaged, such as interstitial pneumonia, adverse proliferation of components of bone marrow, retinitis, lymphadenitis, persistent hepatitis, and splenomegaly; and (3) EBV-DNA can be detected in damaged tissues and peripheral blood. With the progress of medical techniques, detections of EBV DNA and RNA in tissues and peripheral blood, histopathology, immunology, etc. have gradually been written into guidelines, but there is still a lack of active and effective treatment.

In addition, there is a specified relationship between EBV infection and immunodeficiency diseases, such as systemic lupus erythematosus (SLE), multiple sclerosis (MS), and X-linked lymphoproliferative diseases (XLP). SLE is a chronic autoimmune disease causing inflammation, and affects the skin, joints, kidneys, heart, lungs, nervous systems, and other organs. Most common signs of SLE include erythema, arthritis, fatigue, and fever. MS is an immune-mediated CNS demyelinating disease. MS is common in young people, can cause severe responses of the CNS, and is often manifested as a recurrent relapse-remission course, which makes conditions of a patient gradually aggravated to cause disability. XLP is an X-linked combined immunodeficiency disease sensitive to EBV infection, and the expression of defective genes, which mainly accumulated in T lymphocytes and NK cells, affects the signal transduction between these cells.

Studies have shown that DCs in patients with the above EBV-associated diseases show a low level of differentiation, a reduced quantity, an impaired ability to recognize and present antigens, and a weak ability to activate naive T cells, so that the body fails to recognize and clear tumor cells finally. EBV infection is very likely one of the reasons for impaired DC functions in associated patients. The above EBV infection-associated diseases can be effectively treated by restoring the number and function of DCs in a patient through a specified technical means. DCs were firstly discovered in 1973 by the Canadian scientist Ralph M. Steinman, one of the winners of the 2011 Nobel Prize in Medicine or Physiology. DCs, named for their dendritic or pseudopod-like protrusions at a mature stage, are the most powerful professional antigen-presenting cells (APCs) currently known in the body, which can efficiently take up, process, and present antigens. DCs are the only APCs found so far that can activate unsensitized naive T cells. In addition, immature dendritic cells (imDCs) show a strong ability to transfer and take up antigens, and mature dendritic cells (mDCs) can effectively activate naive T cells and are in a central link for initiating, regulating, and maintaining an immune response. DCs comprise <1% of total peripheral blood mononuclear cell (PBMC) fraction, but there are abundant antigen-presenting molecules (such as MHC-I and MHC-II), costimulatory factors (such as CD80/B7-1, CD86/B7-2, and CD40), and adhesion factors (such as ICAM-1, ICAM-2, ICAM-3, LFA-1, and LFA-3) on the surface of DCs. Therefore, DCs are an important subset of innate immune cells and professional APCs, and play a key regulatory role in the activation of an immune response in the body and in the maintenance of immune tolerance.

As the most powerful APCs, DCs can effectively present antigen to T cells and induce the activation of T cells, thereby causing a series of immune responses. MHC molecule on the surface of DCs can bind to antigens to form a peptide-MHC complex, thereby presenting antigen signals to T cells. Some costimulatory factors (such as CD80/B7-1, CD86/B7-2, and CD40) highly expressed on DCs provide a second signal necessary for activation of T cells. DCs can also directly present an antigenic peptide to $CD8^+$ T cells, and activate $CD8^+$ T cells with the help of $CD4^+$ T cells. Activated DCs can secrete IL-12, IL-18, chemotactic cytokines (CCKs), etc. in large quantities to activate the proliferation of T cells and initiate an MHC-class I-restricted cytotoxic T lymphocyte (CTL) response and an MHC-class II-restricted $CD4^+$ Th1 immune response. In addition, DCs can activate Perforin P, granzyme B, and FasL/Fas-mediated pathways to enhance NK cytotoxicity, thereby enhancing the body's anti-tumor immune response to facilitate the tumor clearance and kill associated virus-infected cells. DCs themselves can serve as a natural immune adjuvant to improve the immune competence of the body by secreting various cytokines, and can also enhance immune responses of various vaccines. Generally, DCs with relevant antigen and vaccine functions, are called DC-based vaccines.

Vaccines are preventive or therapeutic biological products for human vaccination, and play an important role in controlling the occurrence and prevalence of infectious diseases. A vaccine with only a single antigen component is called a monovalent vaccine, which can only prevent one type of infectious diseases or one type of pathogen infections. A vaccine prepared by mixing two or more types of antigen components in an appropriate ratio is called a multivalent vaccine or combined vaccine. For example, there are more than 100 types of human papillomavirus (HPV), while most only cause skin warts, and only some can cause cervical cancer. The bivalent HPV vaccine can only prevent the infection of HPV 16 and 18 (high-risk HPV), and 70% of cervical cancers are caused by these two types of HPV. The quadrivalent HPV vaccine can prevent the infection of HPV 16, 18, 6, and 11. The nine-valent HPV vaccine can prevent the infection of HPV 16, 18, 31, 33, 45, 52, 58, 6, and 11.

The development of multivalent vaccines has a history of nearly a hundred years, and the research on multivalent vaccines began as early as the 1930s. In 1945, the trivalent influenza vaccine was approved for use in the United States for the first time. Then, the hexavalent pneumococcal vaccine, the Diphtheria-Tetanus (DT) double vaccine, the Diphtheria-Pertussis-Tetanus (DPT) triple vaccine, and the trivalent oral poliovirus attenuated live vaccine were successively developed. Results of clinical trials have shown that the combined immunization with a multivalent vaccine is often superior to the multiple times of vaccination with a monovalent vaccine. When a multivalent vaccine is used for combined immunization, immunization effect of the multivalent vaccine is similar to or better than that of a monovalent vaccine, without any increase in the side effects.

Traditional surgery, radiotherapy, and chemotherapy cause damage to the body of a patient to some extent. The excessive radiotherapy and chemotherapy will shorten the survival time of a patient. The long-term drug treatment may lead to dependence and seriously reduce the life quality of a patient. At present, there is no safe and effective treatment clinically for EBV-associated infectious diseases, and it is urgent to find a novel therapeutic drug or method. Compared with the traditional treatment methods, the immunotherapy gradually becomes a novel cancer treatment method due to its prominent therapeutic effects and low side effects, where DC-based vaccines are playing an increasingly important role. For example, the patent 201911127136.8 discloses an EBV-associated antigen short peptide and a use thereof. The short peptide shows a high affinity with MHC-I and MHC-II molecules on DCs, can effectively make DCs play a role of antigen presentation, and shows a prominent potential for preparation of polypeptide vaccines and DC-based vaccines.

The patent 202011263782.X discloses an EBV epitope and a use thereof. The EBV epitope has strong immunogenicity. After the EBV epitope is transfected into DCs through an adeno-associated viral vector, an antigen gene is expressed in the DCs, and a corresponding antigen protein is presented to T cells through a direct or cross-presentation pathway to induce killer T cells that can specifically kill EBV. Therefore, the EBV epitope is of great significance in the treatment of EBV antigen-positive diseases.

At present, although there are more and more studies on DC-based vaccines, monovalent DC-based vaccines often exhibit limited therapeutic effects. Although different antigen types and antigen combinations can be used to treat various diseases, single antigen can easily lead to immune escape of EBV-infected cells, and a resulting immune response cannot successfully kill infected cells, resulting in unsatisfactory therapeutic effects. In addition, because many heterogeneous cells in vivo can secrete a variety of cytokines that inhibit the maturation of DCs, there is a relatively small number of DCs at the diseased site, and the anti-tumor immune response induced by DCs in the absence of strong tumor antigen stimulation cannot lead to a very significant therapeutic effect in a host. Therefore, it is urgent to develop DC-based vaccines loaded with tumor antigen composites to treat EBV-associated infectious diseases.

SUMMARY

In view of the deficiencies of the prior art, the present disclosure is intended to provide EBV antigen composites and a DC-based vaccine, and a use thereof. In the present disclosure, patient-derived DCs are stimulated in vitro, loaded with a variety of cell lysates with strong immunogenicity for different EBV-infected cells (lysates of human immortalized B lymphoblastoid cell lines (B-LCLs) derived from different EBVs such as SNU-719, YCCEL1, GD1, B95-8, M81, and HKNPC1-9, or lysates of EBV-positive infected cells such as C666-1, HNE1, or EB-3), and induced into mDCs by various cytokines and specific agonists, so as to obtain a complete DC-based vaccine with corresponding tumor antigens. The DC-based vaccine can be injected back into the patient to activate the immune system, stimulate innate immunity (such as inducing NK cells), and stimulate lymphocytes to produce an acquired immune response and produce cytotoxic T cells, thereby accurately killing EBV-infected cells to allow personalised treatment. Compared with radiotherapy and chemotherapy, the DC-based vaccine can be prepared in about one week with a low cost, is safe, and shows no obvious side effects.

In order to achieve the above objective, the present disclosure adopts the following technical solutions.

In an aspect, the present disclosure provides EBV antigen composites, including lysates of human immortalized B-LCLs infected with EBV and/or lysates of various types of EBV-positive infected cells.

Specifically, the human immortalized B-LCLs are one type or a combination of two or more types of GD1, B95-8, M81, HKNPC1-9, SNU-719, and/or YCCEL1 cells; and the EBV-positive infected cells are one type or a combination of two or more types of C666-1, HNE1, EB-3, and/or other EBV-infected cells.

Further specifically, the other EBV-infected cells include T cells, NK cells, or B cells.

In an aspect, the present disclosure provides a use of the EBV antigen composites in preparation of a DC-based vaccine.

In an aspect, the present disclosure provides a DC-based vaccine loaded with the EBV antigen composites described above.

In particular, the DC-based vaccine is a monovalent DC-based vaccine or a multivalent DC-based vaccine.

Specifically, the DC-based vaccine is loaded with one type, two types, or more types of lysates of human immortalized B-LCLs and/or lysates of EBV-positive infected cells.

Further specifically, the human immortalized B-LCLs are one type or a combination of two or more types of GD1, B95-8, M81, HKNPC1-9, SNU-719, and/or YCCEL1 cells; and the EBV-positive infected cells are one type or a combination of two or more types of C666-1, HNE1, EB-3, and/or other EBV-infected cells.

Specifically, an amount of each type of cells in the EBV antigen composites is $2.5 \times 10^7$ to $2.5 \times 10^9$.

Specifically, the DC-based vaccine further includes a primary adjuvant or a cytokine for auxiliary therapy.

Further specifically, the primary adjuvant may be any one of PloyI:C, LPS, or OK432; and the cytokine for auxiliary therapy may be TNF-α or IL-12.

In an aspect, the present disclosure provides a use of the EBV antigen composites or the DC-based vaccine in preparation of a drug for preventing and/or treating an EBV-associated infectious disease.

Specifically, the EBV-associated infectious disease includes, but is not limited to, IM, CAEBV infection, EBV-HLH, and an EBV-associated hematologic disease.

The DC-based vaccine provided by the present disclosure can stimulate an immune response of the body to treat an EBV-associated infectious disease, especially IM, CAEBV infection, EBV-HLH, and other EBV-associated hematologic diseases, with prominent effectiveness and low side effects. The DC-based vaccine can effectively inhibit the proliferation of EBV-associated infected cells and reduce disease progression, and can even achieve complete remission.

In some embodiments, an antigen-sensitized DC population may be an immunogenic composition, and the DC population has been loaded with corresponding antigens. Specific antigens include lysates of human immortalized B-LCLs derived from different EBVs such as GD1, B95-8, M81, HKNPC1-9, SNU-719, and YCCEL1, and lysates of C666-1, HNE1, EB-3, and other EBV-infected cells. Populations of these different cells range from $2.5 \times 10^7$ to $2.5 \times 10^9$ specifically. In some other aspects of the present disclosure, the DC-based vaccine loaded with the EBV antigen composites may be a monovalent DC-based vaccine loaded with a lysate of only one type of EBV-infected cells or a lysate of LCLs, or a multivalent DC-based vaccine loaded with lysates of two types of EBV-infected cells or a lysate of LCLs, or a multivalent DC-based vaccine loaded with lysates of three or more types of EBV-infected cells or a lysate of LCLs.

In some aspects, the DC-based vaccine of the present disclosure may include a primary adjuvant (such as Ploy(I:C), LPS, and OK432) or a cytokine (such as TNF-α or IL-12) for auxiliary therapy. The DC-based vaccine may be administered intravenously, intradermally, intratumorally, intramuscularly, intraperitoneally, intranodally, subcutaneously, or topically 3 to 30 times at an interval of one or two weeks; and the DC-based vaccine may be injected each time at a cell amount of $1 \times 10^6$ cells to $5 \times 10^8$ cells.

In an aspect, the present disclosure provides a drug for prevention and/or treatment of an EBV-associated infectious disease, including the DC-based vaccine described above.

COMPARED WITH THE PRIOR ART, THE PRESENT DISCLOSURE HAS THE FOLLOWING POSITIVE AND BENEFICIAL EFFECTS

The DC-based vaccine can fight against a disease by activating the immune system of a patient. Compared with the traditional treatment for EBV-associated infectious diseases, the DC-based vaccine has the following advantages:

1. The DC-based vaccine of the present disclosure is safe when used for treating an EBV-associated infectious disease.

The surgery, chemotherapy, or radiotherapy will terribly harm the body of a patient and severely reduce the immune resistance to cancer cells while killing virus-infected cells or cancer cells. Due to the tumor heterogeneity of patients, most anticancer drugs, especially the new generation of targeted drugs, are only effective for a small number of patients, and the drug resistance is easily developed, resulting in a high cancer recurrence rate. Compared with the traditional chemotherapy or targeted therapy, the DC-based vaccine provides a new idea for treatment of tumors. The DC-based vaccine directly targets immune cells in vivo and kills cancer cells by activating the immune system, which does not cause direct damage, but strengthens the immune system. The DC-based vaccine can inhibit the evolution of cancer cells, leads to a low recurrence rate, and has significantly less side effects than the traditional chemotherapy and multi-targeted drugs as a whole. For example, the multivalent DC-based vaccine works by activating the immune system, and thus merely has the most common side effects of clinical class I/II adverse reactions, such as fever, fatigue, dizziness, systemic muscle soreness, and drowsiness, which can be treated symptomatically. Therefore, the DC-based vaccine has a promising clinical application prospect.

2. The selection of antigens for the multivalent DC-based vaccine of the present disclosure is effective for treatment of EBV-associated infectious diseases.

In most of the current projects in which the DC-based vaccine is used to treat an EBV-associated disease, a specific polypeptide is adopted as an antigen. The multivalent DC-based vaccine of the present disclosure has a variety of EBV-infected cell lysates, so that all antigens for activating immune responses against cancer cells are included and the actual EBV antigen in the human body is loaded to the maximum extent, which enhances the diversity of antigen presentation by DCs, maximizes the activation of human immune functions, and can induce a strong T cell response, thereby enhancing a therapeutic effect.

3. Cell lysates used for the multivalent DC-based vaccine of the present disclosure are derived from stable EBV-infected cell lines and EBV-positive infected cells. In this way, there is no need for time-consuming and labor-intensive screening EBV antigens for each patient. The cell lysates are universal antigens because of no HLA restriction. Such antigens can be easily prepared with a simple process and a whole preparation cycle of only one week, which saves several months compared with the preparation of a neoantigen DC-based vaccine.

The EBV-infected cell lysates can have a uniform quality, which avoids the complicated antigen-screening process, and brings outstanding advantages in reducing costs and saving time.

4. The multivalent DC-based vaccine of the present disclosure has a long-lasting therapeutic effect and can effectively inhibit the recurrence and metastasis of an EBV-associated disease for a long time. After being injected into a patient, the multivalent DC-based vaccine can make a large number of memory T lymphocytes carrying abundant EBV antigen produced in vivo, which can exist for several years to several decades. When encountering corresponding stimulation once again, the memory T lymphocytes can be rapidly activated to kill EBV-infected cells, which can effectively prevent the recurrence and metastasis of EBV.

DETAILED DESCRIPTION OF THE EMBODIMENTS

Figure 1:
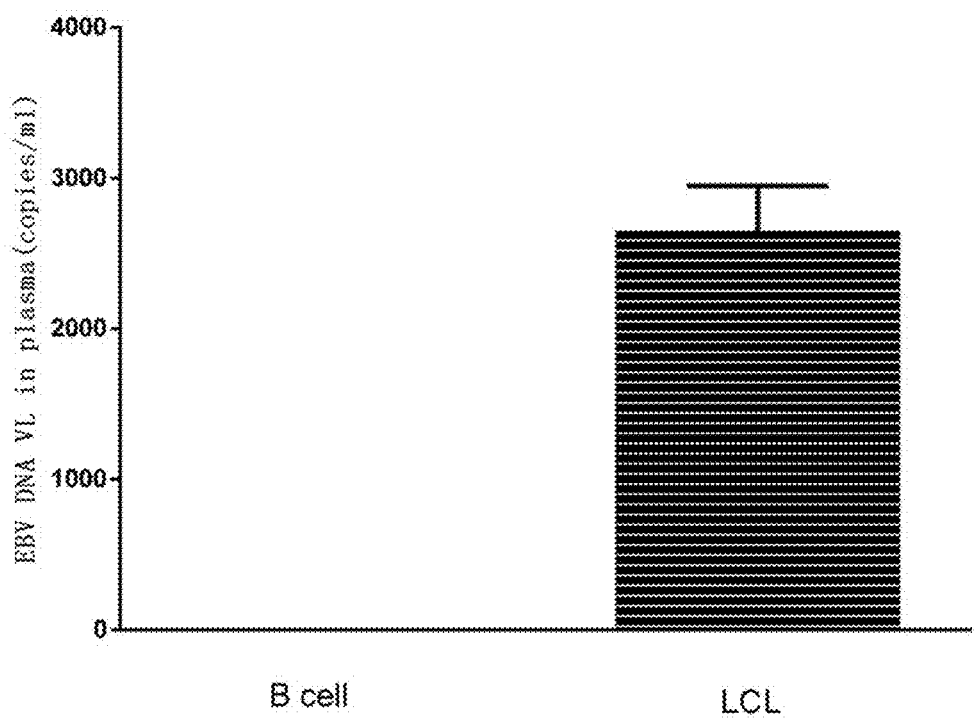
FIG. 1 shows detection results of EBV loads in human immortalized B-LCLs.

The present disclosure is further described in detail below in conjunction with specific examples, and these examples are not intended to limit the present disclosure and are merely intended to illustrate the present disclosure. The experimental methods used in the examples are conventional, unless otherwise specified; the experimental methods without specified conditions in the examples are generally conducted under conventional conditions; and the materials, agents, or the like used in the examples are generally commercially available, unless otherwise specified.

Example 1. Isolation of PBMCs

In this example, based on density differences among cell components in peripheral blood (the peripheral blood mainly includes platelets, mononuclear cells, granulocytes, and erythrocytes, where a density of the platelets is 1.030 kg/m$^3$ to 1.035 kg/m$^3$, a density of the mononuclear cells is 1.075 kg/m$^3$ to 1.090 kg/m$^3$, a density of the granulocytes is 1.092 kg/m$^3$, and a density of the erythrocytes is 1.093 kg/m$^3$), the Ficoll® Paque Plus (GE Healthcare) solution (with a density of 1.075 kg/m$^3$ to 1.089 kg/m$^3$) was added to a peripheral blood sample, and then the density gradient centrifugation was conducted, so that different cell components were separated into different layers and thus the mononuclear cells could be quickly isolated from human peripheral blood.

(1) Peripheral blood was collected from a vein of an EBV-infected patient into a centrifuge tube with an appropriate specification, and 4.5 mL of a Ficoll® Paque Plus solution was added by a pipette to another two centrifuge tubes, respectively.

(2) A blood sample was slowly added to an upper layer of the Ficoll solution along a wall of the centrifuge tube by a pipette, with 10 mL per centrifuge tube. Then the centrifuge tubes were centrifuged at room temperature and 800 g for 20 min.

(3) The centrifuge tubes were taken out, in which the Ficoll® Paque Plus isolated cells top to down, as follows: a plasma layer, a mononuclear cell layer, a Ficoll® Paque Plus® layer, a granulocyte and erythrocyte layer.

(4) The mononuclear cell layer was carefully transferred to a 15 mL centrifuge tube, a phosphate buffered saline (PBS)/1% fetal bovine serum (FBS) solution was added to 14 mL, and a resulting mixture was pipetted up and down for thorough mixing and then centrifuged at room temperature and 800 g for 5 min.

(5) A resulting supernatant was discarded, a bottom of the centrifuge tube was flicked to loosen cells, then 14 mL PBS/1% FBS solution was added to resuspend the cells, and a resulting mixture was pipetted up and down for thorough mixing and then centrifuged at room temperature and 700 g for 5 min.

(6) A resulting supernatant was discarded, a bottom of the centrifuge tube was flicked to loosen cells, then 14 mL RPMI/10% FBS solution was added to resuspend the cells, and a resulting mixture was pipetted up and down for thorough mixing and then centrifuged at room temperature and 400 g for 5 min.

(7) A resulting supernatant was discarded, a bottom of the centrifuge tube was flicked to loosen the cells, then 10 mL RPMI/10% FBS solution was added to resuspend the cells, and a resulting mixture was pipetted up and down for thorough mixing.

(8) 10 μL of a resulting cell suspension was transferred to a 1.5 mL centrifuge tube, and 90 μL of an RPMI/10% FBS solution was added to dilute the cell suspension 10-fold. 10 μL of a diluted cell suspension was taken and mixed with 10 μL of Trypan Blue for staining, and the resulting mixture was added to a hemacytometer and counted under an inverted microscope.

(9) The remaining cell suspension was centrifuged at room temperature and 700 g for 5 min, a resulting supernatant was discarded, and an appropriate amount of PBS/1% FBS was added for subsequent experiments.

Example 2. Construction of Human Immortalized B-LCLs Infected with EBV (1) 10 mL of a culture supernatant of B95-8 cells was transferred to a centrifuge tube and centrifuged at 2,000 rpm for 15 min, and a resulting supernatant was filtered.

(2) The PBMCs prepared in Example 1 were resuspended in 2 mL of an RPMI1640/10% FBS medium.

(3) 10 μL of a resulting cell suspension was taken, diluted 10-fold with 90 μL of RPMI/10% FBS, and then counted under a microscope. According to a counting result, a required volume of a filtered B95-8 supernatant was calculated, where every 1×10$^6$ PBMCs corresponded to 1 mL of the filtered B95-8 supernatant.

(4) PBMCs were collected and centrifuged at 1,000 rpm for 5 min, and a resulting PBMC supernatant was discarded.

(5) According to a cell counting result, the PBMCs were resuspended with an appropriate amount of the filtered B95-8 supernatant to obtain a cell suspension in which a concentration of the PBMCs was 5×10$^5$/500 μL.

(6) A sterile 96-well plate was prepared, and the suspension of PBMCs in the filtered B95-8 supernatant was added to the 96-well plate at 100 μL/well.

(7) The 96-well plate was incubated in a CO$_2$ incubator for 24 h.

(8) The 96-well plate was taken out, then 100 μL of an R10 medium (RPMI1640/10% FBS, 1,000 U/mL penicillin, and 100 μg/mL streptomycin) was added to each well, and a resulting mixture was pipetted up and down for thorough mixing.

(9) The 96-well plate was further incubated in an incubator for 6 d, during which a cell status was observed every day to determine whether the cell status underwent the following lymphoblastoid changes: increased cell volume, enriched cytoplasm, spherical shape, aggregated distribution of small colonies, significantly increased cell masses at a bottom of the well, and yellowing medium.

(10) After the 6-d cultivation was completed, the medium was changed every 3 d. The upper medium in each well was carefully removed, then 100 μL of an R10 medium was added to each well, and the cells were further cultivated. When the medium turned yellow, the medium was changed timely, or the cells were dispensed into another 2 to 4 wells as required, and after the number of cells gradually increased, the cells were then combined and transferred to a 24-well plate, a 6-well plate, and a T25 flask in sequence.

(11) A status of cells cultivated for 4 weeks was observed under a microscope, and it could be known that human immortalized B-LCLs infected with EBV were prepared.

Normal B cells and the immortalized human B-LCL infected with EBV prepared in the present disclosure were tested by real-time fluorescent quantitative polymerase chain reaction (Q-PCR) to detect the expression of an EBNA1 gene, thereby reflecting the load or expression level of EBV.

Detection of EBV viral loads (VLs) of cells: DNA was extracted with the MagMAX Viral Nucleic Acid Extraction Kit (Thermo A42352) and subjected to PCR with the EBV Real-TM Quant Kit (Sacace BioTechnologies Srl, Como, Italy), and 10 μL of a sample was taken and tested by real-time quantitative PCR (EBV Real-TM Quant Kit) to detect the VLs of EBV. In this experiment, a coding region of the EBNA1 gene was selected as an amplification target, β-actin was adopted as an internal reference gene, and the PCR was conducted according to instructions with a final volume of 25 μL. Primer sequences were as follows:

EBNA1-FP:
5'-CCAGACAGCAGCCAATTGTC-3', as shown in SEQ ID NO: 1;

-continued

EBNA1-RP:
5'-GGTAGAAGACCCCCTCTTAC-3', as shown in SEQ ID
NO: 2;

β-actin-FP:
5'-CTCCATCCTGGCCTCGCTGT-3', as shown in SEQ ID
NO: 3;
and

β-actin-RP:
5'-GCTGTCACCTTCACCGTTCC-3', as shown in SEQ ID
NO: 4.

Detection results of the VLs of EBV were shown in FIG. 1. EBV VLs of the normal B cells was almost undetectable, and EBV VLs of the human immortalized B-LCLs prepared in the present disclosure was much higher than EBV VLs of the normal B cells.

Similarly, other EBV-infected cells such as GD1, B95-8, M81, HKNPC1-9, SNU-719, and YCCEL1 could be used to prepare human immortalized B-LCLs infected with corresponding EBVs according to the steps in this example, these cell lines were tested, and test results showed that EBV VLs of these cell lines were much higher than the EBV VLs of the normal B cells.

Example 3. Preparation of a Lysate of EBV-Infected Cells

The repeated freezing-thawing method is a common mechanical lysis method, which usually consists of freezing and thawing. A principle of the method is as follows: The generation of intracellular ice particles and the increase of a salt concentration in the remaining cell solution cause swelling, so that a cell structure is broken and cells die, but the immunogenicity of the cells is retained. The freezing is usually conducted in liquid nitrogen or at −20° C., and the thawing can be conducted through heat shock in a water bath at 37° C., 50° C., 65° C., or 100° C., which is milder than the chemical lysis.

(1) A temperature of a water bath was pre-set to 37° C.
(2) Human immortalized B-LCL cells or EBV-positive infected cells (such as C666-1, HNE1, EB-3, or other EBV-infected T cells, NK cells, or B cells) (at least $3 \times 10^7$ cells) were collected through centrifugation at room temperature and 700 g for 5 min.
(3) A resulting supernatant was discarded, and resulting cells were resuspended in RPMI/10% FBS to obtain a cell suspension.
(4) The cells were counted with trypan blue.
(5) The cell suspension was centrifuged at room temperature and 700 g for 5 min, and a resulting supernatant was carefully removed.
(6) Resulting cells were resuspended with RPMI/10% FBS in a 1 mL freezing tube, with a density of $5 \times 10^6$/mL.
(7) The cells were frozen in liquid nitrogen for 20 s.
(8) The cells were immediately thawed quickly and completely in a 37° C. water bath.
(9) Steps (7) and (8) were repeated 4 times, that is, steps (7) and (8) were conducted 5 times in total.
(10) A lysate of EBV-infected cells was stored in liquid nitrogen before use.

Example 4. Preparation of imDCs

1. Isolation of CD14$^+$ Monocytes
Methods for isolating CD14 monocytes include, but are not limited to, magnetic-activated cell sorting (MACS) in this example, CD14 negative selection and cell attachment. The isolation principle of MACS is based on the specific binding of antigens and antibodies. Human CD14 magnetic beads can specifically recognize and bind to human CD14$^+$ cells among PBMCs, and the magnetic beads are indirectly coupled with biotin or dextran, so that the CD14$^+$ cells can be separated under the affection of a high-intensity magnetic field. In this example, the EasySep™ CD14 positive selection kit was adopted.

(1) A PBMC suspension was transferred to a 5 mL FAC tube.
(2) An appropriate amount of a selection cocktail solution was added to the FAC tube with a final concentration of 100 μL/mL, and a resulting mixture was pipetted up and down for thorough mixing and then incubated at room temperature for 10 min.
(3) Preparation of magnetic beads: a RapidSphere™ solution was vortexed for 30 s, so that the magnetic beads were dispersed evenly.
(4) An appropriate amount of a RapidSphere™ solution was added to the FAC tube with a final concentration of 100 μL/mL, and a resulting mixture was pipetted up and down for thorough mixing and then incubated at room temperature for 3 min.
(5) An appropriate amount of PBS/2% FBS solution with 1 mM EDTA was added to the FAC tube until a total volume was 2.5 mL, and a resulting mixture was pipetted up and down for thorough mixing.
(6) The FAC tube was vertically inserted into the EasySep™ magnet and incubated for 3 min at room temperature.
(7) A magnet was placed invertedly, and a cell solution flowing out from the FAC tube was collected into a 15 mL centrifuge tube, where the magnet was placed invertedly for 3 s, and the tube should not be shaken or a liquid on a wall of the tube should not be totally removed.
(8) The magnet was placed upright and then the FAC tube was taken out.
(9) Steps (7) and (8) were repeated two times.
(10) 2 mL of RPMI/10% FBS was added to the FAC tube to resuspend cells, and the cells were counted with Trypan Blue.

2. Induction of CD14$^+$ Monocytes to Produce imDCs
In vitro, granulocyte-macrophage colony-stimulating factor (GM-CSF) can promote the survival of imDCs and induce the massive proliferation of imDCs. IL-4 can inhibit the overgrowth of macrophages, reduce the expression of CD14 on cells, and induce the differentiation of CD14$^+$ monocytes into iDCs.

(1) In a clean bench, a CD14$^+$ cell suspension was transferred by a pipette to each well in a 6-well plate with a concentration of $2 \times 10^6$ cells/mL, and then 1 μL of human recombinant GM-CSF (final concentration: 2,000 IU/mL, Miltenyi, 170-076-112) and 1 μL of human recombinant IL-4 (final concentration: 1,000 IU/mL, Miltenyi, 170-076-101) were added to the 6-well plate.
(2) The 6-well plate was placed on a surface of the clean bench, then gently shaken three times back and forth and three times left and right to make the cells dispersed evenly, and incubated in a cell incubator at 37° C. and 5% $CO_2$ for 3 d.
(3) The 6-well plate was taken out from the incubator, and then 2 mL of RPMI1640/10% FBS, 1 μL of human recombinant GM-CSF (final concentration: 2,000 IU/mL, Miltenyi, 170-076-112), and 1 μL of human recombinant IL-4 (final concentration: 1,000 IU/mL, Miltenyi, 170-076-101) were added to the 6-well plate in a clean bench.

(4) The plate was incubated in an incubator at 37° C. and 5% $CO_2$ for 2 d to obtain imDCs.

Example 5. Loading of a Lysate of EBV-Infected Cells to Prepare a Multivalent DC-Based Vaccine (1) Preparation of a Monovalent DC-Based Vaccine (Take Human Immortalized B-LCLs Prepared with B95-8 Named B95-8-LCL as an Example):

imDCs were co-cultivated with the lysate of B95-8-LCL for 6 h, then 2 μL of TNF-α (final concentration: 2,000 IU/mL, Miltenyi, 170-076-103), 2 μL of LPS (final concentration: 2 μg/mL, Sigma, L4391), and 1 μL of Poly(I:C) (1 μg/mL, Sigma, P1530) were added to stimulate the maturation of DCs, and resulting mDCs were prepared into the monovalent DC-based vaccine, which was denoted as Ag-DC.

Similarly, corresponding monovalent DC-based vaccines could be prepared with lysates of GD1-LCL, M81-LCL, HKNPC1-9-LCL, SNU-719-LCL, YCCEL1-LCL, C666-1, HNE1, EB-3, or other EBV-infected T cells, NK cells, and B cells.

(2) Preparation of a Multivalent DC-Based Vaccine:

DCs were co-cultivated with each of lysatates of different EBV-infected cells such as EBV-infected B lymphocytes, T cells, and NK cells, C666-1, HNE1, EB-3, GD1-LCL, M81-LCL, HKNPC1-9-LCL, SNU-719-LCL, YCCEL1-LCL, or B95-8-LCL for 6 h, then 2 L of TNF-α (final concentration: 2,000 IU/mL, Miltenyi, 170-076-103), 2 μL of LPS (final concentration: 2 μg/ml, Sigma, L4391), and 1 μL of Poly(I:C) (1 μg/mL, Sigma, P1530) were added to stimulate the maturation of DCs, and resulting multiple types of DCs loaded with EBV-infected cell antigen were mixed in equal amounts in a DC medium to obtain the multivalent DC-based vaccine loaded with lysate antigens of EBV-infected cells, which was denoted as Poly-DC (in this example, a multivalent DC-based vaccine prepared with lysates of EBV-infected B lymphocytes and B95-8-LCL cells was taken as an example).

Figure 2:
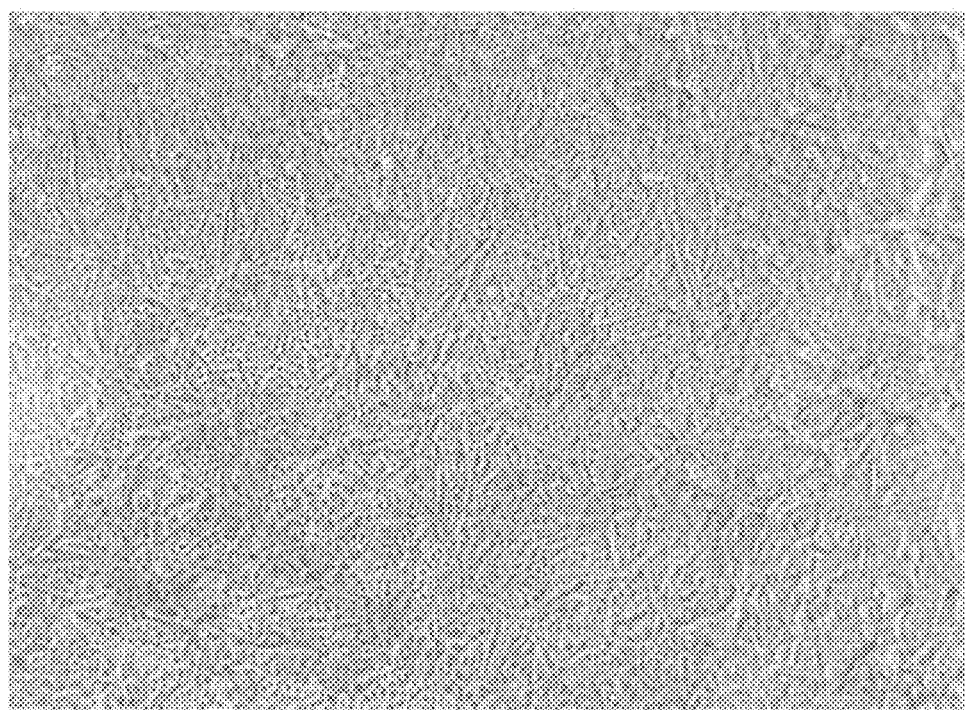
FIG. 2 shows the morphology of mDCs.

(3) Observation of morphology of mDCs as shown in FIG. 2, a culture dish of mDCs was placed under an optical microscope (10× objective lens) and observed, and it could be seen that the mDCs grew adherently, and had increased long protrusions radially distributed on their surfaces, indicating an obvious dendritic shape; and at a high density, various cells were connected to each other to form a network structure.

Figure 3:
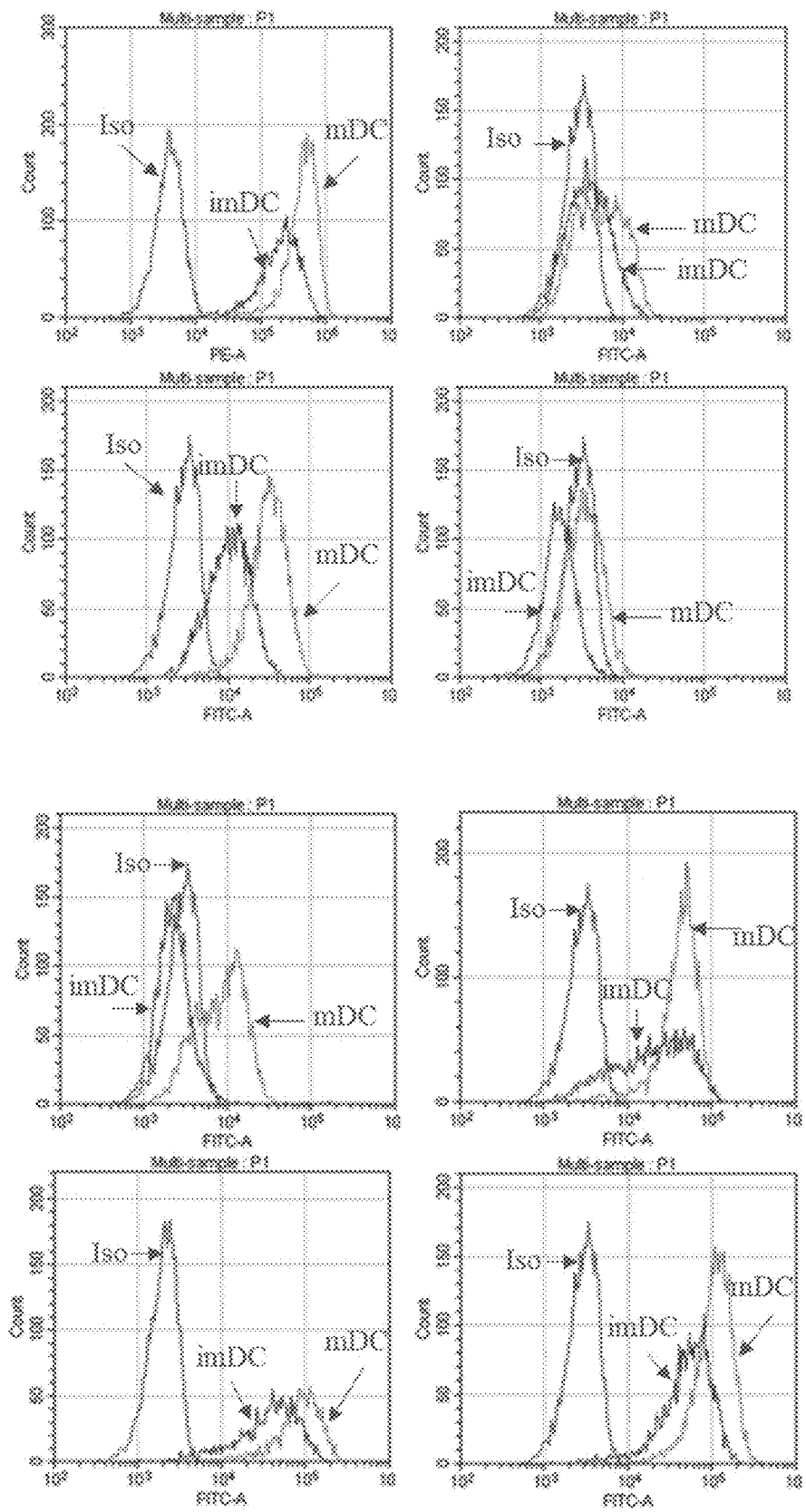
FIG. 3 shows flow cytometry (FCM) results of expression levels of surface markers on DCs.

(4) Surface markers CD11c, CD14, CD40, CD80, CD83, CD86, HLA-DR, and HLA-ABC on imDCs and mDCs were detected by FCM. Detection results were shown in FIG. 3 (where Iso represents an FCM pattern of a corresponding antibody isotype control, imDC represents an FCM pattern of molecules on the surface of imDCs, and mDC represents an FCM pattern of molecules on the surface of mDCs). It can be seen from this figure that expression levels of molecules CD11c, CD14, CD40, CD80, CD83, CD86, HLA-DR, and HLA-ABC on the surface of mDCs were higher than that on the surface of imDCs, indicating that imDCs had been induced into mDCs.

(5) Culture supernatants of imDCs and mDCs were collected, and the expression of IL-12p70 secreted by DCs was detected by enzyme-linked immunosorbent assay (ELISA).

Figure 4:
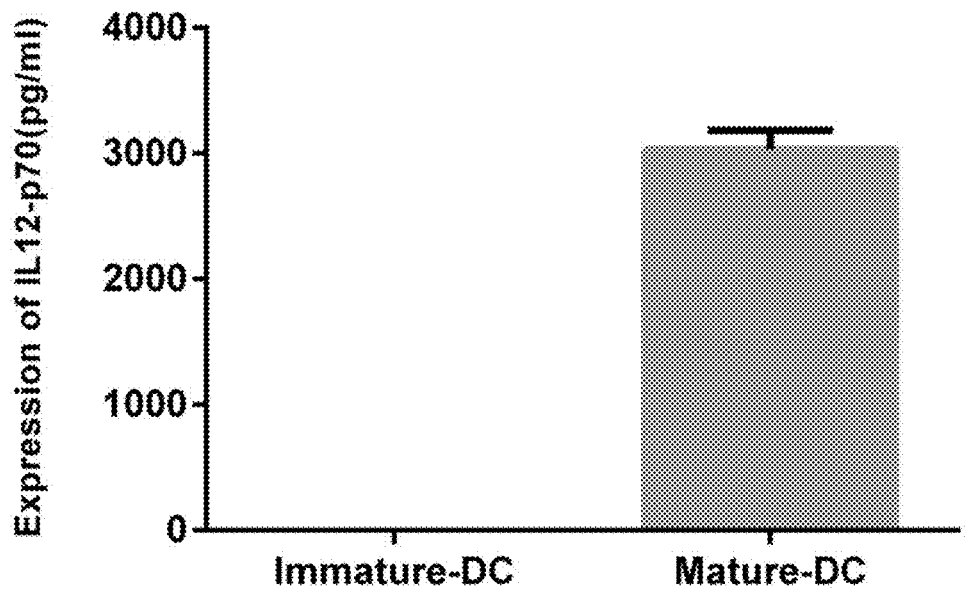
FIG. 4 shows detection results of expression levels of IL-12p70 in DCs.

Detection results were shown in FIG. 4, and it could be seen from this figure that imDCs secreted almost no IL-12p70, and after imDCs were induced to mature, the secretion of IL-12p70 were enhanced.

Experimental Example 1

1. Preparation of T Lymphocytes (1) The PBMCs prepared in Example 1 were cultivated in an incubator at 37° C. and 5% $CO_2$ for 2 h, and then suspended cells were collected and prepared into 1 mL of a cell suspension.

(2) The cell suspension was added to a nylon wool fiber column incubated at 37° C., the column was laid flat, then 200 μL of pre-warmed 10% FBS-containing RPMI 1640 was added for sealing, and then the column was statically incubated at 37° C. for 2 h.

(3) The nylon wool fiber column was subjected to elution with 10% FBS RPMI 1640 at a flow rate of about 1 mL/min, and 10 mL of a cell suspension obtained at the beginning was collected, which contained abundant T cells and NK cells.

(4) The cell suspension was centrifuged at room temperature and 700 g for 5 min, and a resulting cell pellet was collected, counted and adjusted to a concentration of $1 \times 10^7$ cells/mL, and placed in 80 IU/mL IL-2-containing RPMI1640 complete medium for later use.

Alternatively, the magnetic bead separation method could be used, that is, T lymphocytes could be isolated through $CD3^+$ magnetic beads. Cells were first incubated with a surface antigen monoclonal antibody (mAb) for 12 min (50 μL of CD3 mouse mAb was used for every $10^7$ cells), then washed and incubated with 100 μL of a biotin-labeled goat anti-mouse secondary antibody for 10 min, then washed and incubated with 25 μL of FITC-labeled streptavidin for 8 min, and then washed and incubated with 100 μL of biotin-labeled magnetic beads for 8 min. After the above reactions were completed, 1 mL of 1% BSA-containing PBS was added for washing, and a resulting mixture was centrifuged at 2,000 r/min for 10 min. T lymphocytes were isolated through immunomagnetic separation of a magnetic cell separator (MACS).

2. Induction of CTLs Through In Vitro Stimulation

The monovalent DC-based vaccine and the multivalent DC-based vaccine prepared in Example 5 and normal mDCs each were resuspended in an RPMI complete medium, with a cell density adjusted to $2 \times 10^5$ cells/mL. The autologous T lymphocyte suspension isolated in step 1 was adjusted with an RPMI complete medium to a cell density of $1.6 \times 10^6$/mL. 1 mL of each of corresponding DCs and T lymphocytes was added in each group.

The same helper cytokines were added in each of the above experimental groups, with an IL-2 content of 1,000 U/mL, an IL-12 content of 1,500 U/mL, a Poly(I:C) content of 10 mg/mL, and a TNF-α content of 1,000 U/mL. Cells were cultivated for 2 weeks in a constant-temperature and constant-humidity incubator at 37° C. and 5% $CO_2$, IL-2 was added with a final concentration of 30 U/mL, then $2 \times 10^5$ corresponding DCs were added in each group for secondary stimulation, and the cells were further cultivated for one week and harvested on day 21 to obtain CTLs.

Figure 5:
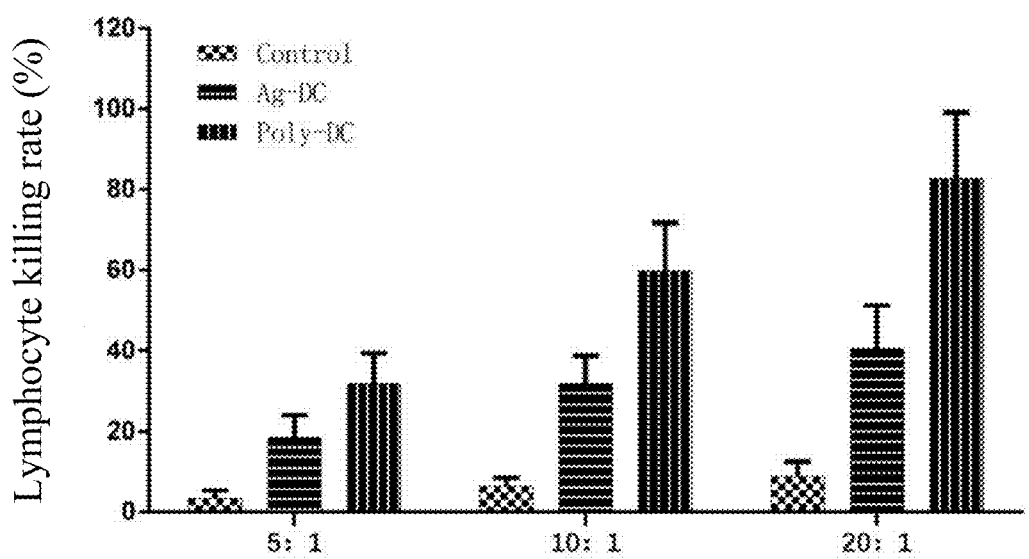
FIG. 5 shows detection results of killing rates of CTL induced by in vitro stimulation.

3. Detection of a Killing Activity of T Cells Stimulated by a DC-Based Vaccine for EBV-Infected Cells The cells obtained in step 2 were centrifuged and resuspended in an RPMI1640 complete medium, a cell concentration was adjusted, and the cells were added as effector cells to a 96-well culture plate at $4 \times 10^5$ cells/well, $2 \times 10^5$ cells/well, and $1 \times 10^5$ cells/well, so as to set three experimental groups with different effector-target ratios. $2 \times 10^4$ LCLs were added as target cells to each well, with a final volume of 200 μL. A blank control group without cells was set. Each of the above groups was conducted for 5 repetitive times. 24 h later, free effector cells in each well were removed, the plate was washed twice with PBS, 100 μL of a reagent including 20 μL of CCK8 was added to each well, and the cells were further cultivated for 2 h. The absorbance (OD) at 450 nm was detected by a microplate reader, and a killing rate (%) of specific lymphocytes was calculated. Detection results were shown in FIG. 5. In vitro, T lymphocytes stimulated by the multivalent DC-based vaccine (Poly-DC group) was compared with T lymphocytes stimulated by the monovalent DC-based vaccine only loaded with a lysate of LCLs (Ag-DC group) or the control group; and in terms of a killing activity of tested cells for LCLs, both the Poly-DC group and the Ag-DC group could effectively kill LCLs and inhibit the proliferation of LCLs, and the poly-DC group of T lymphocytes stimulated by the multivalent DC-based vaccine exhibited a stronger killing ability against LCLs, where the more the T lymphocytes, the more significant the killing effect.

Figure 6:
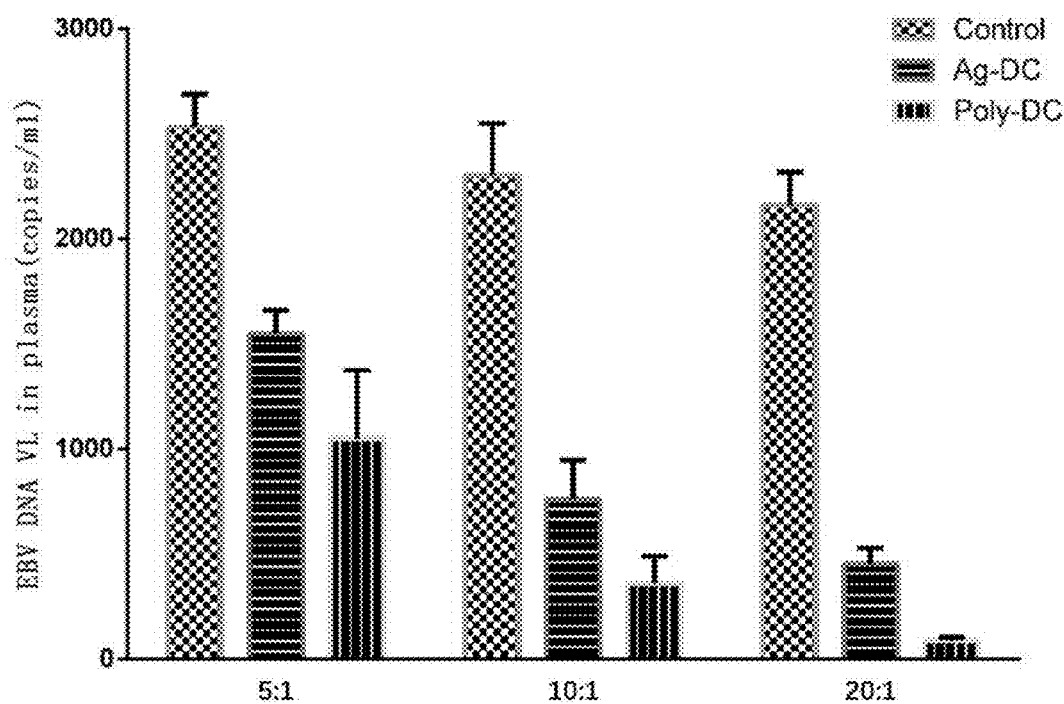
FIG. 6 shows detection results of EBV loads in LCLs after cocultivation.

The expression of EBV in LCLs was detected by real-time fluorescent quantitative PCR, and detection results were shown in FIG. 6. T lymphocytes stimulated by the multivalent DC-based vaccine (Poly-DC group) was compared with T lymphocytes stimulated by the monovalent DC-based vaccine loaded with a lysate of LCLs (Ag-DC group) or the control group; and in terms of an EBV load in LCLs in each group, EBV loads in LCLs in the Poly-DC group and the Ag-DC group were significantly lower than that in the control group, and an EBV load in LCLs at each T cell effector-target ratio in the Poly-DC group was lower than that in the Ag-DC group, indicating that the T lymphocytes stimulated by the multivalent DC-based vaccine could effectively inhibit EBV gene expression of LCLs, kill LCLs, and inhibit the proliferation of EBV-positive cells.

4. In Vitro Detection of IFN-γ Secretion

Figure 7:
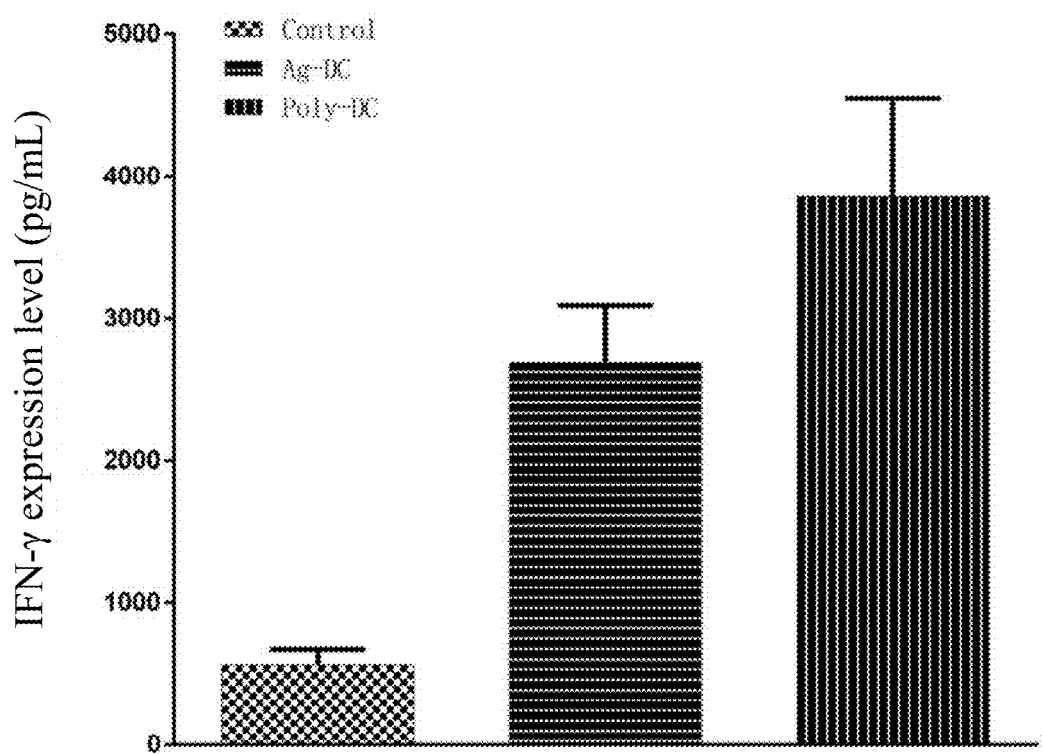
FIG. 7 shows detection results of secreted IFN-7.

The effector CTLs and LCLs in each group obtained in step 2 were mixed in a U-bottom 96-well plate according to an effector-target ratio of 20:1 and cultivated for 72 h, and a content of IFN-γ in a culture supernatant was detected with an IFN-γ ELISA kit according to instructions. Detection results were shown in FIG. 7. T lymphocytes stimulated by the monovalent DC-based vaccine (Ag-DC group) and T lymphocytes stimulated by the multivalent DC-based vaccine (Poly-DC group) could produce a large amount of IFN-γ, and a content of IFN-γ in each of the two groups was significantly higher than that in the control group; and a content of IFN-γ secreted by T cells in the Poly-DC group was higher than that in the Ag-DC group, indicating that the multivalent DC-based vaccine loaded with lysates of EBV-positive cells could intensely stimulate the differentiation of T lymphocytes to secrete IFN-γ and promote the anti-EBV infection ability of the body.

The above examples merely represent several implementations of the present disclosure, and the descriptions thereof are specific and detailed, but these examples should not be construed as limiting the patent scope of the present disclosure. It should be noted that those of ordinary skill in the art can further make several variations and improvements without departing from the concept of the present disclosure, and all of these fall within the protection scope of the present disclosure. Therefore, the protection scope of the present disclosure shall be subject to the protection scope defined by the claims.

What is claimed is:

1. A method for treating an Epstein-Barr virus (EBV)-associated infectious disease, comprising: administering to a subject a dendritic cell (DC)-based vaccine loaded with EBV antigen composites, wherein the EBV-associated infectious disease comprises infectious mononucleosis (IM), chronic active EBV (CAEBV) infection, and EBV-associated hemophagocytic lymphohistiocytosis (EBV-HLH);

the EBV antigen composites comprise lysates of human immortalized B lymphoblastoid cell lines (B-LCLs) B95-8-LCL, GD1-LCL, M81-LCL, HKNPC1-LCL to HKNPC9-LCL, SNU-719-LCL, YCCEL1-LCL, and lysates of EBV positive infected cells C666-1, HNE1, and EB-3;

wherein a method for preparing the DC-based vaccine comprises:

(1) induction of immature DC (imDC): transferring a CD14$^+$ cell suspension to a well plate with $2 \times 10^6$ cells/mL in each well, and then adding human recombinant granulocyte-macrophage colony-stimulating factor (GM-CSF) to a final concentration of 2,000 IU/mL and human recombinant interleukin (IL)-4 to a final concentration of 1,000 IU/mL to the well plate for induction to prepare imDC;

(2) induction of mature DC (mDC): co-cultivating the EBV antigen composites with imDC in step (1), adding tumor necrosis factor (TNF)-α to a final concentration of 2,000 IU/mL, LPS to a final concentration of 2 μg/mL and Poly(I:C) to a final concentration of 1 μg/mL to stimulate a maturation of imDC, wherein an amount of cells for producing each of the lysates is $3 \times 10^7$; and (3) detection of induced mDCs: measuring an increase in cell surface markers CD11c, CD40, CD80, CD83, CD86, HLA-DR, and HLA-ABC in the mDC compared to the imDC by flow cytometry (FCM).

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: The sequence is synthetized

<400> SEQUENCE: 1
ccagacagca gccaattgtc                                              20

<210> SEQ ID NO 2
<211> LENGTH: 20
<212> TYPE: DNA
<213> ORGANISM: Artificial Sequence
<220> FEATURE:
<223> OTHER INFORMATION: The sequence is synthetized

<400> SEQUENCE: 2
ggtagaagac cccctcttac                                              20

<210> SEQ ID NO 3
<211> LENGTH: 20
<212> TYPE: DNA
<213> ORGANISM: Artificial Sequence
<220> FEATURE:
<223> OTHER INFORMATION: The sequence is synthetized

<400> SEQUENCE: 3
ctccatcctg gcctcgctgt                                              20

```
<210> SEQ ID NO 4
<211> LENGTH: 20
<212> TYPE: DNA
<213> ORGANISM: Artificial Sequence
<220> FEATURE:
<223> OTHER INFORMATION: The sequence is synthetized

<400> SEQUENCE: 4
gctgtcacct tcaccgttcc                                           20
```